(12) United States Patent
Wire

(10) Patent No.: US 10,130,776 B2
(45) Date of Patent: Nov. 20, 2018

(54) PROTECTIVE SUPPORT FOR NEEDLES

(71) Applicant: James P. Wire, Chaska, MN (US)

(72) Inventor: James P. Wire, Chaska, MN (US)

(*) Notice: Subject to any disclaimer, the term of this patent is extended or adjusted under 35 U.S.C. 154(b) by 69 days.

(21) Appl. No.: 15/090,590

(22) Filed: Apr. 4, 2016

(65) Prior Publication Data

US 2017/0080162 A1 Mar. 23, 2017

Related U.S. Application Data

(60) Provisional application No. 62/145,274, filed on Apr. 9, 2015.

(51) Int. Cl.
*A61M 5/32* (2006.01)
*A61M 5/34* (2006.01)

(52) U.S. Cl.
CPC .......... *A61M 5/3213* (2013.01); *A61M 5/344* (2013.01)

(58) Field of Classification Search
CPC ............ A61M 2005/3247; A61M 5/32; A61M 5/3213; A61M 2005/3215
See application file for complete search history.

(56) References Cited

U.S. PATENT DOCUMENTS

| | | | |
|---|---|---|---|
| 4,485,918 A | 12/1984 | Mayer | |
| 4,596,562 A | 6/1986 | Vernon | |
| 4,610,667 A * | 9/1986 | Pedicano | A61M 5/002 604/192 |
| 4,659,330 A | 4/1987 | Nelson et al. | |
| 4,664,259 A | 5/1987 | Landis | |
| 4,717,386 A | 1/1988 | Simmons | |
| 4,900,309 A * | 2/1990 | Netherton | A61M 5/3213 336/192 |
| 4,915,698 A | 4/1990 | Levenson | |
| 4,938,514 A | 7/1990 | D'Addezio | |
| 4,955,866 A | 9/1990 | Corey | |
| 4,986,817 A * | 1/1991 | Code | A61M 5/3213 604/192 |
| 5,037,400 A | 8/1991 | Curry | |
| 5,078,696 A * | 1/1992 | Nedbaluk | A61M 5/3213 604/192 |
| 5,186,712 A * | 2/1993 | Kelso | A61M 25/0606 604/157 |
| 5,195,982 A | 3/1993 | Hoenig | |
| 5,300,039 A * | 4/1994 | Poulsen | A61M 5/3243 604/198 |
| 5,334,151 A * | 8/1994 | Santilli | A61M 5/3213 206/365 |
| 5,429,611 A * | 7/1995 | Rait | A61M 5/3257 604/110 |
| 5,514,117 A * | 5/1996 | Lynn | A61M 5/158 604/536 |
| 5,564,565 A * | 10/1996 | Yamada | A61M 5/3213 128/919 |

(Continued)

FOREIGN PATENT DOCUMENTS

WO 8912474 12/1989
WO 2013016109 1/2013

*Primary Examiner* — Scott Medway
(74) *Attorney, Agent, or Firm* — Dicke, Billig & Czaja, PLLC

(57) ABSTRACT

Apparatus for supporting implements such as hypodermic syringes. The structure is made so as to protect operators against inadvertent sticking and the possible consequences thereof.

9 Claims, 3 Drawing Sheets

(56) References Cited

U.S. PATENT DOCUMENTS

| | | | |
|---|---|---|---|
| 6,206,855 B1 * | 3/2001 | Kunkel | A61M 5/3213 |
| | | | 206/365 |
| 6,659,983 B2 * | 12/2003 | Crawford | A61B 5/15003 |
| | | | 604/177 |
| 6,878,131 B2 | 4/2005 | Novacek et al. | |
| 6,916,392 B2 | 7/2005 | Trpkovski et al. | |
| 8,282,662 B2 | 10/2012 | Reaux | |
| 8,317,743 B2 * | 11/2012 | Denenburg | A61J 1/2096 |
| | | | 604/518 |
| 2009/0014462 A1 * | 1/2009 | Costa | A61M 5/3205 |
| | | | 221/185 |

* cited by examiner

PROTECTIVE SUPPORT FOR NEEDLES

This is a United States national patent application filed pursuant to 35 USC § 111(a) claiming priority under 35 USC § 120 of U.S. Pat. Appl. Ser. No. 62/145,274 having a filing date of Apr. 9, 2015 and entitled PROTECTIVE SUPPORT FOR HYPODERMIC SYRINGES, the disclosure of which is hereby incorporated by reference in its entirety.

TECHNICAL FIELD

The present invention is relevant to the practice of medicine. A specific embodiment of the invention deals with a tool usable in the practice of medicine. The specific focus of the invention is a guard for hypodermic needles to minimize hazards to personnel who utilize such needles.

BACKGROUND OF THE INVENTION

The present invention relates to structures for rendering needles safe for presentation and use, and, more particularly, to a device designed to facilitate encapsulation of a needle attached to a syringe, and, alternatively, to enable removal of a cap to expose the needle allowing use of the syringe.

Hypodermic syringes are widely used in response to their necessity in many medical and surgical procedures. One unfortunate aspect of such needles is that they can expose the operator to the risk of injury from the needles. Beyond an immediate and painful injury, this risk can entail infection due to fluid-borne pathogen exposure.

The risk of injury can be reduced by encapsulating the needle attached to the syringe with a removable cap. Typically, removal of the cap for use of the syringe is accomplished with relative ease and only slight risk. In contrast, replacement of the cap is more difficult and exposes the user to greater risk of injury. Further, should there be the need or desire to recap a needle during a medical procedure, the attention demanded may distract the physician or other user from the procedure at hand.

To counteract these difficulties, standards for medical procedures do require that surgical needles be discarded after a single use, thus avoiding some of the risk associated with recapping the needle. Such standards can be impractical, however, in procedures that require multiple injections. These procedures can require refilling syringes and passing them uncapped through the operating field.

One device intended to facilitate the recapping of a hypodermic needle is disclosed in a patent application published under the Patent Cooperation Treaty (International Publication No. WO 2013/016109). The device of that document takes the form of a substantially planar substrate having an opening with a plurality of flexible flaps formed about its periphery. The flaps cooperate to releasably support a needle cap inserted through the opening. To remove a cap from a capped needle and syringe, the user inserts the cap through the opening and grips it by hand on one side of the planar substrate, while withdrawing the syringe and needle with the other hand on the other side of the substrate.

To recap the syringe after use, the substrate (with the cap retained in the opening) is held in one hand while the other hand is used to align the needle with the open end of the cap. The needle is then inserted into the cap by moving the syringe toward the substrate.

The substrate device reduces the risk of inadvertent, injurious contact with the tip of a hypodermic needle. At the same time, however, needle alignment and insertion require careful attention, especially close visual tracking, as the physician or other user attempts to recap the needle by guiding the exposed needle to the opening in the substrate and the cap held thereby. Insertion of a capped needle and syringe into the substrate opening likewise requires the physician's full and direct attention. Each of these tasks optimally requires the use of both hands.

SUMMARY OF THE INVENTION

To address these concerns, the present invention provides a device for safely supporting a hypodermic needle and syringe. The preferred device includes a unitary body, somewhat large in comparison to the syringe. Accordingly, it provides stable support for the syringe on a table or other generally flat surface or in the hand of the operator. The device preferably is formed of plastic, but aluminum, stainless steel or medical grade plastic can both increase the stability it provides and withstand multiple sterilizations.

With regard to its shape, the device is extended along an axis, with a bell portion generally narrowing in the direction from its proximal end to its distal end. The proximal end of the bell is provided with one or more cuts each along a corresponding chord in the bell. Such cuts prevent the device from rolling when it is placed on a flat surface. A longitudinally extending needle cap receiver is formed along a distal portion of the device. The receiver is open at its distal end to a proximal interior guide region of the device. The receiver has a transverse profile that conforms to the profile of a standard needle cap used as protective covering for a hypodermic needle. As a result, insertion of the standard needle cap into the receiver forms a secure frictional engagement of the cap within the device.

The proximal interior guide region is defined by a bell inner guide surface that diverges from the receiver to a guide opening at the proximal end of the device. The guide surface preferably is formed as a truncated cone disposed with respect to the longitudinal axis of the device. As a result, when the distal end of a needle and/or syringe (whether or not capped) is inserted into the device via the guide opening, it is moved toward the receiver by the guide surface as the syringe is moved longitudinally into the device. Thus, distal insertion of the syringe tends to center the tip of the needle or cap relative to the receiver as the syringe is inserted.

In preferred versions, the receiver can be formed as a passage extending substantially completely through the device. The length of the passage is typically shorter than the standard needle cap. In addition, the receiver can be shaped to accept cap insertion to the point that a proximal end of the cap is aligned with or disposed slightly distally of the guide surface adjacent the receiver.

This arrangement affords several advantages. One arises from the fact that a fully inserted needle cap protrudes distally of the distal end of the device. As a result, the fully inserted cap can be removed from the device by moving the device toward a stationary surface (e.g., a table surface) with the distal end of the cap pressed against the surface. Moving the device with sufficient force overcomes the frictional engagement with the cap thus releasing the capped needle from the device.

Another advantage arises from the location of the cap proximal end when the cap is fully inserted. To recap a syringe, the user inserts the exposed needle tip into the bell. As the syringe is moved distally into the bell, the bell inner surface encounters the needle tip and moves it toward alignment with the receiver and the cap. The proximal edge of the cap, either aligned with or disposed slightly distally of the guide surface, cooperates with the guide surface to guide the needle tip into the cap opening to facilitate insertion of the needle into the cap.

The device is particularly useful in procedures that require multiple injections, because it enables and facilitates repeated episodes of cap removal and cap replacement without requiring the full or focused attention of the user. Between successive uses, the device provides a stable and reliable support for the capped syringe.

BRIEF DESCRIPTION OF THE DRAWINGS

For a further understanding of the above and other features and advantages, reference is made to the following detailed description and to the drawings, in which.

DETAILED DESCRIPTION OF THE INVENTION

Figure 1:
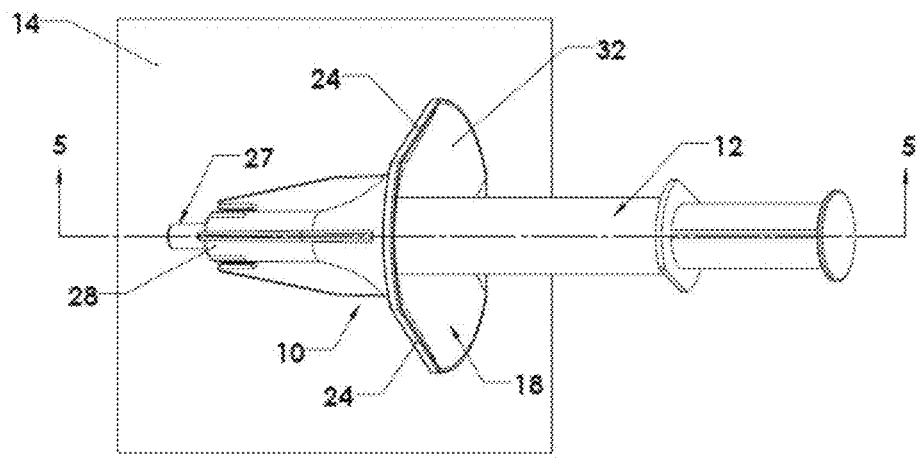
FIG. 1 is a top perspective view of a device for supporting, capping and uncapping hypodermic needles attached to syringes constructed according to the present invention.
Figure 2:
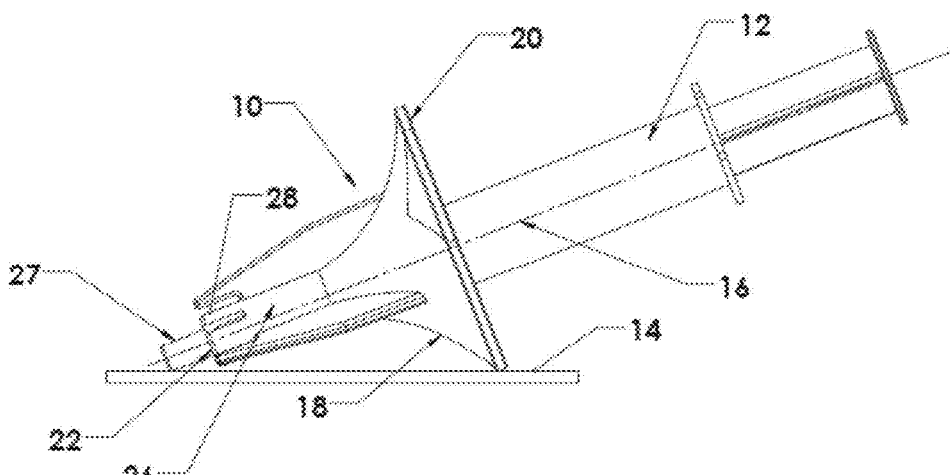
FIG. 2 is a side elevation of the device.
Figure 3:
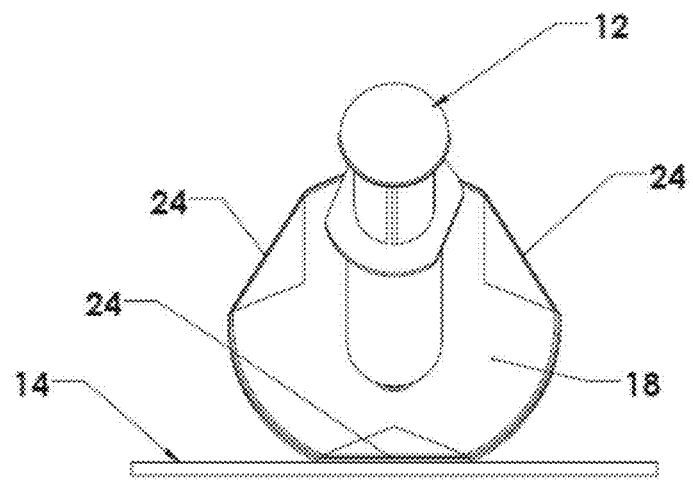
FIG. 3 is a forward elevation of the device.
Figure 4:
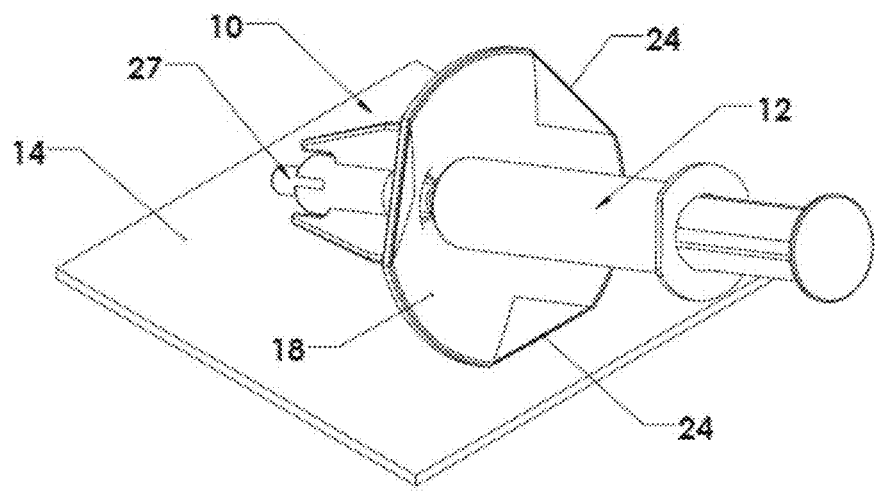
FIG. 4 is an oblique perspective view of the device.
Figure 5:
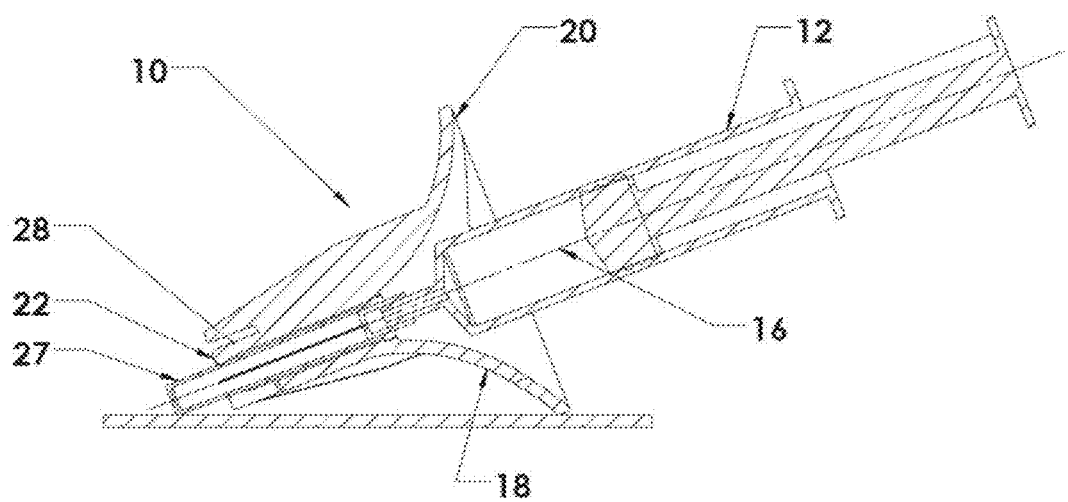
FIG. 5 is a cross-sectional view of the device, taken along the line 5-5 of FIG. 1.

Referring now to the drawing figures wherein like reference numerals denote like elements throughout the several views, FIGS. 1-5 show a device 10 for safely supporting a capped needle syringe 12, for example. Although the support functions best in an environment in which the surface 14 on which the device 10 is placed is substantially planar, as illustrated in the figures, the device 10 will function to some degree even if the surface 14 is, for example, somewhat arcuate (not shown). It will be understood, therefore, that the support surface 14 should be sought to be substantially planar and oriented generally horizontally. Such a configuration of the support surface 14 would provide the highest degree of stability as will be seen hereinafter.

The device 10 is formed relative to an axis 16 with a bell portion 18 of the device 10 generally narrowing in a direction from its proximal end 20 to its distal end 22. The proximal end 20 of the bell 18 can be provided with one or more cuts each along a different chord 24 in the perimeter of the bell 18. Such cuts, it is intended, are substantially straight so as to extend along its own chord cut. Such cuts serve to prevent the device from rolling when it is placed on the planar surface 14.

A longitudinally extending needle receiver 26 is formed along the device 10. The receiver 26 is open at its distal end 22 to the interior of the bell 18. The receiver 26 has an interior profile along its distal end 22 which conforms generally to the profile of a standard cap 27 used as a protective covering for a hypodermic syringe needle 12. As a result, when a standard-sized cap is inserted fully into the receiver 26, a secure friction fit will exist between the cap 27 and the interior of the receiver 26 within the device 10. The receiver 26 can comprise a plurality of cantilevered fingers 28 mounted biased generally radially inward so as to exert an inward force upon the cap 27.

The proximal guide region is characterized as a bell 18, and the bell has an inner surface 32 that diverges from the receiver 26 to a guide opening at the distal end 20 of the device 10. The guide surface 32 can preferably be formed in the shape of a truncated cone. The cone-shape bell 18 is formed, it is intended, with respect to the longitudinal axis 16 of the device 10. As a result, the distal end of the capped needle and carried syringe can be inserted into the device 10 with engagement with the interior surface 32 of the bell 18. Thus, when the distal end of a capped needle and syringe is inserted into the device 10 via the guide surface 32, the distal end of the capped needle and syringe 12 is guided radially inward toward the receiver by the guide surface 32. As will be able to be seen in view of this disclosure, insertion of the syringe tends to center the tip of the needle or cap relative to the receiver 26 as the needle and syringe or capped needle and syringe is inserted through the bell 18.

In one preferred embodiment, the receiver 26 can be formed as a passage extending substantially completely axially through the device. It will be understood, in view of this disclosure, that the length of the passage through the bell 18 is typically shorter than the standard needle cap 27. In the embodiment discussed hereinbefore, the receiver 27 can have a shape so as to accept cap insertion to the point that a proximal end of the cap is aligned with, or disposed slightly distally of, the guide surface of the receiver formed by the bell. Such a construction affords several advantages. One will see that a fully inserted needle cap protrudes distally from the distal end of the device 10. Consequently, the fully inserted cap 27 can be removed from the device 10 by moving the device toward a stationary surface (not shown) with the distal end of the cap pressed against the surface. Such engagement renders sufficient force being brought to bear upon the cap 27 to dislodge the cap from the receiver.

Such a construction results in another advantage. To again cap the needle, the user merely need insert the exposed needle tip into the bell 18. As the syringe 12 is moved distally in the bell 18, the bell 18 inner surface 32 is encountered by the needle tip, and the surface 32 moves the needle tip toward alignment with the receiver 26 and the cap 27. The distal edge of the cap cooperates with the guide surface to guide the needle tip into the cap opening. Insertion of the needle into the cap is thereby facilitated.

The device defined hereinbefore is preferably made of plastic. Aluminum, stainless steel and medical grade plastic all can function to increase the stability provided and withstand multiple sterilizations.

It will be understood that this disclosure, in many respects, is only illustrative. Changes may be made in details, particularly in matters of shape, size, dimensions, material, and arrangement of parts without exceeding the scope of the invention. Accordingly, the scope of the invention is as defined in the language of the appended claims.

What is claimed is:

1. A device for supporting a syringe needle assembly, the syringe needle assembly including a needle mounted to a syringe, and a needle cap selectively received over the needle, the device comprising:

a bell portion having a bell shape and defining an inner guide surface having a diameter that tapers from a proximal end; and a receiver extending from the bell portion opposite the proximal end, wherein the receiver terminates at a distal end opposite the bell portion;

wherein the receiver includes a tube portion defining an aperture extending from the distal end and open to the inner guide surface, the aperture sized to receive the needle cap of the syringe needle assembly, wherein a profile of the aperture differs from a profile of the inner guide surface of the bell portion;

and further wherein the receiver includes a plurality of longitudinal slots formed in the tube portion at the distal end to define a plurality of fingers for capturing the needle cap, wherein respective ones of the fingers are defined between a corresponding pair of the slots, and further wherein the fingers are longitudinally spaced from the bell portion; and even further wherein the receiver comprises a plurality of slats each projecting radially outwardly from an exterior of the tube portion, each of the slats having a cantilevered portion extending longitudinally over and radially spaced from a corresponding one of the fingers.

2. The device of claim 1, wherein the bell portion includes a generally conical wall having a circle-defining periphery.

3. A device in accordance with claim 2 wherein said periphery includes arcuate portions and portions which are chords of a circle.

4. A device in accordance with claim 3 wherein said arcuate portions and said portions which are chords of a circle alternate circumferentially.

5. The device of claim 1, wherein the slats of the plurality of slats are circumferentially spaced from one another.

6. The device of claim 5, wherein an exterior surface of the tube portion is accessible at a gap between circumferentially adjacent ones of the slats.

7. The device of claim 1, wherein each of the slats extend to the bell portion.

8. The device of claim 7, wherein a gap is defined between the each of the fingers and the corresponding slat at the distal end.

9. The device of claim 1, wherein the device is configured to facilitate repeated usages of the syringe needle assembly by releasable retention of the needle cap.

\* \* \* \* \*